United States Patent [19]

Kalopissis et al.

[11] 3,972,937
[45] Aug. 3, 1976

[54] DIPHENYLAMINES FOR DYEING KERATINOUS FIBERS

[75] Inventors: Gregoire Kalopissis, Paris; Andrèe Bugaut, Boulogne-sur-Seine; Francoise Estradier, Paris, all of France

[73] Assignee: L'Oreal, Paris, France

[22] Filed: Aug. 21, 1974

[21] Appl. No.: 499,189

Related U.S. Application Data

[60] Division of Ser. No. 270,633, July 11, 1972, Pat. No. 3,853,464, which is a continuation-in-part of Ser. No. 61,833, Aug. 6, 1970, Pat. No. 3,792,090.

[30] Foreign Application Priority Data

Aug. 11, 1969 Luxemburg............................ 59265
July 14, 1971 Luxemburg............................ 63526

[52] U.S. Cl.................................. 260/571; 8/10.2; 8/11; 260/562 R; 260/562 A
[51] Int. Cl.²............................................ C07C 91/42
[58] Field of Search........................ 260/571, 562 A

[56] References Cited
UNITED STATES PATENTS

| | | | |
|---|---|---|---|
| 1,806,040 | 5/1931 | Byers.............................. | 260/571 X |
| 2,101,879 | 12/1937 | Strouse............................ | 260/571 |
| 2,692,262 | 10/1954 | Bosshard......................... | 260/571 X |
| 3,219,704 | 11/1965 | Wilder et al..................... | 260/571 X |
| 3,458,577 | 7/1969 | Galantay......................... | 260/571 |
| 3,787,174 | 1/1974 | Kalopissis et al............... | 260/571 X |
| 3,792,090 | 2/1974 | Kalopissis et al............... | 260/571 |
| 3,853,464 | 10/1974 | Kalopissis et al............... | 260/571 X |

OTHER PUBLICATIONS

Voller, Chemistry of Organic Compounds, W. B. Saunders, Co. p. 761 (1966).
House, Modern Synthetic Reactions, 2nd Ed., W. A. Benjamin, Inc., p. 1408 (1972).

*Primary Examiner*—Helen M. S. Sneed
*Attorney, Agent, or Firm*—Cushman, Darby & Cushman

[57] ABSTRACT

Hair dye and hair-setting lotion compositions contain a diphenylamine of the formula

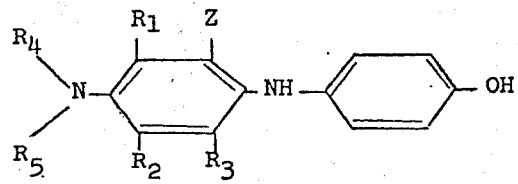

wherein Z represents amino, acylamino or hydroxy, $R_1$, $R_2$ and $R_3$ represent hydrogen or lower alkyl, $R_4$ represents hydrogen, lower alkyl or together with $R_1$ and the nitrogen atom to which $R_4$ is attached form a dihydro-oxazine or pyrroline heterocycle and $R_5$ represents hydrogen, lower alkyl or together with $R_2$ and the nitrogen atom to which $R_5$ is attached form a dihydro-oxazine or pyrroline heterocycle and the acid salts of said diphenylamine.

3 Claims, No Drawings

DIPHENYLAMINES FOR DYEING KERATINOUS FIBERS

This is a division of application Ser. No. 270,633, filed July 11, 1972, now U.S. Pat. No. 3,853,464, which is a continuation-in-part of application Ser. No. 61,833, filed Aug. 6, 1970, now U.S. Pat. No. 3,792,090.

This invention relates to novel leuco derivatives of indoanilines, a process for preparing the same end to novel cosmetic compositions containing these leuco derivatives for dyeing keratinic fibers such as human hair. The leuco derivatives of indoanilines of this invention are colorless compounds which, when applied in an aqueous solution to the fibers to be dyed, oxidize in the air or in the presence of another oxidizing agent, thereby giving the corresponding indoanilines, which on the other hand are colored compounds directly responsible for dyeing of the fiber. The dyeings thus obtained present qualities of fastness and intensity of dyeing superior to those dyeings obtained by direct application of indoanilines, because of the better solubility of the leucoderivatives of these compounds.

More specifically the present invention relates to novel dyeing compositions for keratinous fibers, in particular for human hair, characterized in that they contain in an aqueous or dilute alcohol solution at least one leucoderivative, i.e., a diphenylamine of the formula

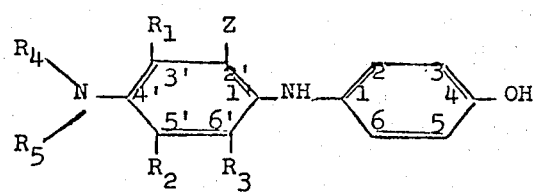

(I)

wherein Z represents a member selected from the group consisting of amino, acylamino and hydroxy; $R_1$, $R_2$ and $R_3$, each independently represent a member selected from the group consisting of hydrogen and lower alkyl containing from 1 to 4 carbon atoms; $R_4$ represents a member selected from the group consisting of the hydrogen, lower alkyl containing 1–4 carbon atoms and together with $R_1$ and the nitrogen atom to which $R_4$ is attached form a heterocycle selected from the group consisting of dihydro-oxazine and pyrroline; and $R_5$ represents a member selected from the group consisting of hydrogen, lower alkyl containing 1–4 carbon atoms and together with $R_2$ and the nitrogen atom to which $R_5$ is attached form a heterocycle selected from the group consisting of dihydro-oxazine and pyrroline; or a salt formed by this leucoderivative with an organic or inorganic acid, particularly, oxalic acid, hydrochloric acid and tartaric acid.

The dyeing compositions according to the invention can contain only the compounds of formula (I), in which case they make it possible to obtain an extremely rich range of shades including violets, blues, greens, reds and pinks, and a great variety of more or less ash, golden or copper blonds. These colorings can develop on the fibers under the sole action of the oxygen in the air, or again under the action of another oxidizing agent such as hydrogen peroxide, the latter being able to be incorporated in the compositions of this invention at the time of their application to the hair.

Because of their affinity for keratinous fibers and the power of the colorings to which they give rise, the compounds of formula (I) can be used in the compositions according to the invention in extremely slight concentrations. These concentrations can vary between 0.002 and 2% by weight and are generally between 0.005 and 0.5% by weight.

The pH of the dye compositions according to the invention can vary between 4 and 11. To regulate this pH at the desired value, it is possible to use as alkalizing agents, ammonia, mono-, di- or triethanolamine, and as acidifying agents, phosphoric acid, acetic acid or lactic acid.

The dye compositions according to the invention can be in aqueous solutions to which, if desired, there can be added low molecular weight alcohols such as ethanol or isopropanol, in amounts of 20 to 70% by weight, or again glycols such as propyleneglycol or butylglycol, in amounts of 1 to 6% by weight. These alcohols and glycols facilitate the use of the diphenylamines of formula (I).

The dye compositions according to the invention can also contain other known leucoderivatives of indoanilines, indamines or indophenols, or again oxidation dyes such as ortho- or paraphenylenediamines or ortho- or para-aminophenols. They can also contain direct dyes such as nitro dyes of the benzene series, azo dyes, anthraquinone dyes, oxazines or azines.

Further the compositions according to the invention can contain various ingredients usually used in capillary cosmetics, such as, wetting agents, dispersing agents, penetrating agents, thickeners or perfumes. They can, on the other hand, be in the form of creams or gels, or packaged under pressure in aerosol bombs or containers, together with a conventional aerosol propellant such as dichlorodifluoromethane, trichloromonofluoromethane and their mixtures. Obviously other conventional aerosol propellants can be used.

Dyeing of keratinous fibers, in particular human hair, with the dye compositions according to the invention, can be performed in the usual way, by application of the composition to the fibers to be dyed, the composition being left in contact with the fibers for a time varying from 10 to 30 minutes. Following this application, the fibers can be rinsed and if desired washed. Thereafter, the thus treated fibers are dried. If desired, there can be added to the composition, before its application, either 20 to 60 percent by weight of the composition of hydrogen peroxide at 20 volumes or equivalent quantities of another oxidizing agent, especially if it is desired to achieve a simultaneous bleaching of the fiber.

In another embodiment of the present invention, the novel diphenylamines can also be employed in the production of capillary hair-setting lotions. These lotions comprise an aqueous alcohol solution, at least one diphenylamine of Formula I or a salt thereof and at least one cosmetic resin. The amount of diphenylamine or its salt present in the hair-setting lotion according to this invention can be extremely slight. Such an amount generally varies between 0.002 and 1% by weight and preferably between 0.002 and 0.5% by weight, of the total hair-setting lotion composition, the pH of which generally lies between 5–8.

Representative cosmetic resins that can be employed in the hair-setting lotions of the present invention include, for instance, polyvinyl pyrrolidone having a molecular weight of 40,000–400,000, copolymer of crotonic acid and vinyl acetate, said copolymer having a molecular weight ranging from about 10,000 to 70,000, copolymer of vinyl pyrrolidone and vinyl acetate wherein the ratio of PVP to VA ranges between 50–70:50–30, said copolymer having a molecular weight ranging from about 30,000 to 200,000 and maleic anhydride-butylvinyl ether copolymers, a 1% solution of which in methylethyl ketone has a viscosity of 0.1 3.5 cps at 25°C. These resins are used in a proportion of 1 to 3% by weight of the hair-setting lotion composition.

The alcohols suitable for the preparation of the hair-setting lotions according to the invention are low molecular weight alkanols, such as ethanol or isopropanol which are present in amounts of about 20 to 70% by weight of the total hair-setting lotion composition.

The hair-setting lotions of the present invention impart to the hair a great variety of hues located in the ash blond, golden blond or copper blond tones, and which can even be shaded violet, mauve, blue, green or pink. The colorings obtained are characterized by a pearly appearance and a great richness of glints and by their regularity, even in the case of application of irregularly bleached hair.

The hair-setting lotions according to the invention are usually employed by application to wet hair, previously washed and rinsed, followed by rolling the hair up on curlers and drying the hair.

Certain of the compounds of formula (I) are novel, and these novel compounds are also a part of the present invention. Thus, the present invention also has as an object, the provision of compounds of the formula

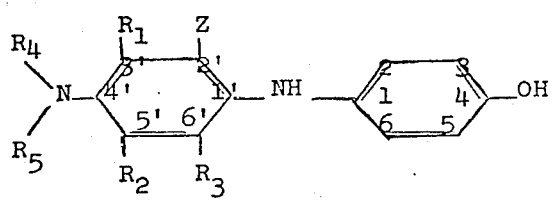

wherein Z represents a member selected from the group consisting of amino, acylamino and hydroxy; $R_1$, $R_2$ and $R_3$ each independently are selected from the group consisting of hydrogen and lower alkyl containing 1–4 carbon atoms; $R_4$ represents a member selected from the group consisting of hydrogen, lower alkyl containing 1–4 carbon atoms and together with $R_1$ and the nitrogen atom to which $R_4$ is attached form a heterocycle selected from the group consisting of dihydro-oxazine and pyrroline; and $R_5$ represents a member selected from the group consisting of hydrogen, lower alkyl containing 1–4 carbon atoms and together with $R_2$ and the nitrogen atom to which $R_5$ is attached form a heterocycle selected from the group consisting of dihydro-oxazine and pyrroline; with the proviso that at least two of $R_1$, $R_2$, $R_3$, $R_4$ and $R_5$ are other than hydrogen when Z is other than acylamino; and a salt formed by this compound with an organic or inorganic acid, particularly, oxalic acid, hydrochloric acid and tartaric acid.

The compounds represented by Formula I, above can be prepared by reducing an indoaniline having the formula

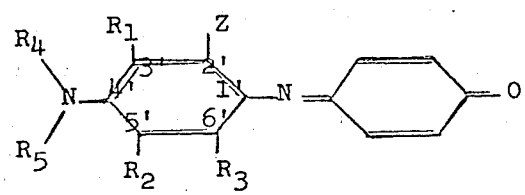

wherein $R_1$ to $R_5$ and Z have the meanings given above, in an aqueous or dilute aqueous alcohol medium having an alkaline pH in the range of about 9 to 12 and in the presence of effective amounts of a reducing agent selected from the group consisting of sodium hydrosulfite or an alkaline sulfide such as ammonium sulfide. The amount of reducing agent can vary but generally it will be present in amounts such that the mole ratio of indoaniline being reduced to reducing agent ranges between 1:1.5 to 1:3. This reducing reaction is generally carried out at ambient pressure and at a temperature ranging from about 25° to 50°C.

Alternatively the reduction of the above indoaniline can be carried out in a solvent selected from the group consisting of ethanol and ethyl acetate by catalytic hydrogenation at ordinary pressure and a temperature of 20° to 50°C in the presence of catalytic amounts of palladium on a substrate selected from the group consisting of barium sulfate and carbon. Generally the amounts of the catalyst, i.e. the palladium on said substrate, ranges between about 10 to 25 percent by weight of indoaniline being reduced.

The following examples are intended to illustrate the present invention. Unless otherwise specified, all parts and percentages are by weight and all temperatures are expressed in degrees centigrade.

EXAMPLE 1

4-hydroxy 2'-amino 4'-N,N-dimethylamino diphenylamine is prepared according to the following reaction:

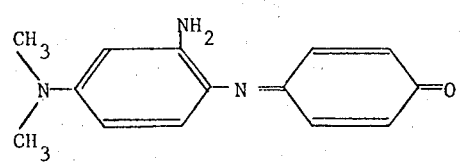

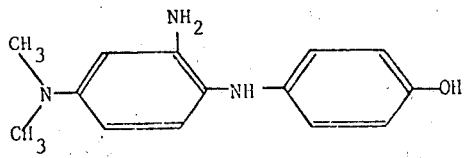 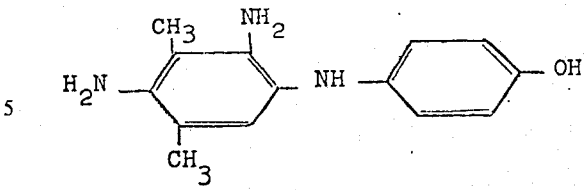

0.0028 mol (0.550 g) of N-[(2'-amino 4'-dimethylamino) phenyl] benzoquinoneimine is dissolved in 200 cc of absolute ethyl alcohol. To the resulting solution, there is added 100 mg. of palladium on carbon (10% Pd on C of "Engelhard Industries") as the catalyst and the product is reduced in the usual way by hydrogen at normal pressure and a temperature of 30°C. After 10 minutes, the reaction medium is colorless. The solution is then filtered to recover the catalyst and the thus filtered solution is concentrated under vacuum and nitrogen up to 50 cc. Then 50 cc of water, saturated with carbon dioxide gas, is added and the above diphenylamine which has precipitated, is filtered therefrom. After drying under vacuum, the above compound exhibits a melting point of 197°C. Molecular weight calculated for $C_{14}H_{17}N_3O$ = 243. Molecular weight found by potentiometric determination in acetic acid by perchloric acid = 245.

| Analysis | Calculated for | Found | |
|---|---|---|---|
| | $C_{14}H_{17}N_3O$ | | |
| C% | 69.11 | 69.02 | 69.23 |
| H% | 7.04 | 6.87 | 6.90 |
| N% | 17.27 | 17.38 | 17.34 |

EXAMPLE 2

4-hydroxy 3', 5'-dimethyl 2',4'-diamino diphenylamine and its dihydrochloride, monohydrate are prepared according to the following reaction:

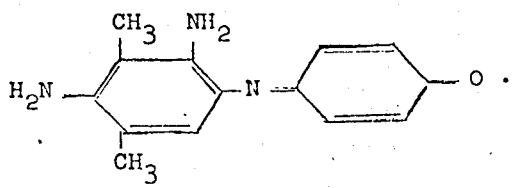

To 150 cc of a 1.25 N soda solution containing 0.05 mole (14 g) of sodium hydrosulfite of 75% purity, there is gradually added, with good stirring, while keeping the reaction mixture in the vicinity of 30°°, 0.02 mole (5.90 g) of N-([2',4'-diamino 3',5'-dimethyl) phenyl] benzoquinoneimine trihydrate partially dissolved in 30 cc of 95° ethanol. When the addition is completed, the reaction mixture is colorless. It is filtered and acetic acid is added to pH 7 to precipitate the above diphenylamine. After filtering, washing with water and drying under vacuum at 80° for 5 hours, the above diphenylamine exhibits a melting point of 220°. Molecular weight calculted for $C_{14}H_{17}N_3O$ = 243. Molecular weight found by potentiometric determination in acetic acid by perchloric acid = 241.

| Analysis | Calculated for | Found | |
|---|---|---|---|
| | $C_{14}H_{17}N_3O$ | | |
| C% | 69.11 | 69.08 | 69.22 |
| H% | 7.04 | 7.02 | 7.06 |
| N% | 17.27 | 17.05 | 17.14 |

1 g of the above diphenylamine thus obtained is dissolved in 10 cc of 2 N hydrochloric solution. The solution is cooled to −10°, then 10 cc of hydrochloric acid at 22°B are added. The 4-hydroxy 3',5'-dimethyl 2',4'-diamino diphenylamine dihydrochloride, monohydrate crystallizes. After filtering and drying under vacuum, the product melts with decomposition at 209°. Molecular weight calculated for $C_{14}H_{17}N_3O \cdot 2\ HCl;\ H_2O$ = 334. Molecular weight found by potentiometric determination in water with 0.1 N soda solution = 332.

EXAMPLE 3

N-[7'-(6'-amino 1'-oxa 4'-aza 1',2',3',4'-tetrahydro)-naphthyl]4-amino phenol is prepared in accordance with the following reaction:

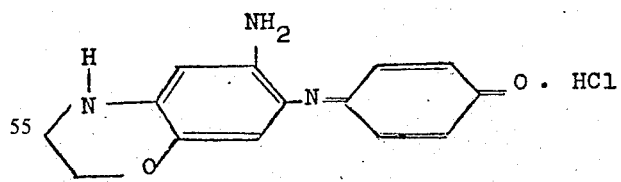

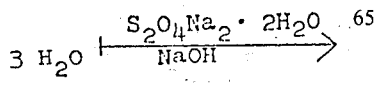 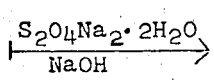

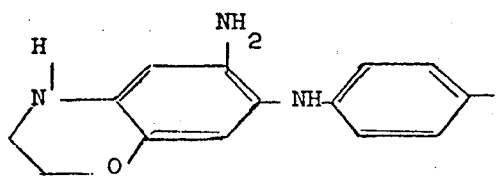

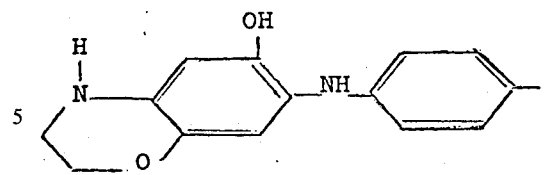

0.05 mole (14 g) of sodium hydrosulfite of 75% purity is dissolved in 160 cc of 1.25 N soda solution. There is then added gradually, with good stirring, while keeping the temperature in the vicinity of 30°, 0.02 mole (5.82 g) of N-[7'-(6'-amino 1'-oxa 4'-aza 1',2',3',4'-tetrahydro)-naphthyl] benzoquioneimine hydrochloride in 30 cc of ethanol and 10 cc of water. When the addition is completed, the reaction mixture is allowed be become colorless. It is cooled, neutralized with acetic acid and the above compound, which has precipitated, is filtered therefrom. After washing with water, saturated with carbon dioxide gas, followed by a recrystallization in a dimethylformamide-water mixture and drying under vacuum for 5 hours at 80°, the above compound exhibits a melting point of 215°C. Molecular weight calculated for $C_{14}H_{15}N_3O_2 \cdot 0.5\ H_2O = 266$. Molecular weight found by potentiometric determination in acetic acid by perchloric acid = 262.

| Analysis | Calculated for | Found | |
|---|---|---|---|
|  | $C_{14}H_{15}N_3O_2 \cdot 0.5H_2O$ | | |
| C% | 63.15 | 63.53 | 63.44 |
| H% | 6.02 | 6.05 | 6.07 |
| N% | 15.79 | 15.83 | 15.63 |

EXAMPLE 4

N-[7'-(6'-hydroxy 1'-oxa 4'-aza 1',2',3',4'-tetrahydro)-naphthyl] 4-amino phenol monohydrate is prepared in accordance with the following reaction:

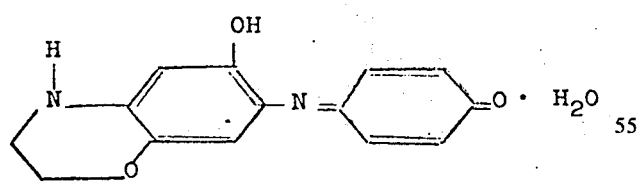

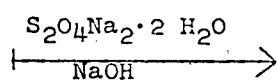

To 75 cc of 1.25 N soda solution, in which there has been dissolved 0.040 mole (10.9 g) sodium hydrosulfite of 75% purity, there is added gradually, with good stirring, while keeping the reaction mixture in the vicinity of 30°, 0.01 mole (2.74 g) of N-[7'-(6'-hydroxy 1'-oxa 4'-aza 1',2',3',4'-tetrahydro)-naphthyl] benzoquinoneimine monohydrate in suspension in 15 cc of ethanol. When the reaction mixture is colorless, it is neutralized with carbonic anhydride to precipitate the above compound. After filtering and drying under vacuum on phosphoric anhydride for 3 days, the above compound exhibits a melting point of 329°C.

| Analysis | Calculated for | Found | |
|---|---|---|---|
|  | $C_{14}H_{14}N_2O_3 \cdot H_2O$ | | |
| C% | 60.86 | 60.93 | 61.03 |
| H% | 5.84 | 5.94 | 5.73 |
| N% | 10.14 | 10.15 | 10.18 |

EXAMPLE 5

4-hydroxy 2'-acetylamino 4'-amino diphenylamine and its dihydrochloride are prepared in accordance with the following reaction:

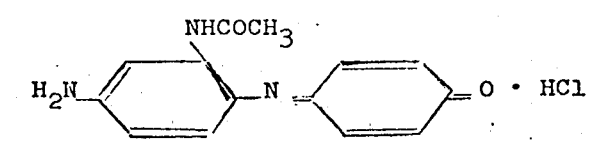

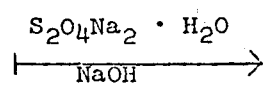

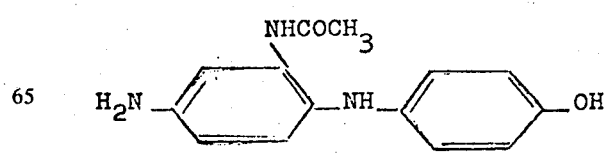

In 100 cc of a normal soda solution, there is dissolved 0.028 mole (8.1 g) of sodium hydrosulfite of 75% purity. To this solution, there is gradually added, while keeping the temperature in the vicinity of 30°, 0.01 mole (2.91 g) of N-[(2'-acetylamino 4'-amino) phenyl] benzoquinoneimine hydrochloride in 20 cc of ethyl alcohol and 5 cc of water. When the reaction mixture is colorless, it is cooled to 0°, then neutralized with acetic acid to precipitate the above compound. This compound is then filtered under nitrogen, washed with water saturated with carbon dioxide gas and dried for 3 days under vacuum on phosphoric anhydride. It melts at 217°. Molecular weight calculated for $C_{14}H_{15}N_3O_2 = 257$. Molecular weight found by potentiometric determination in acetic acid by perchloric acid = 258.

| Analysis | Calculated for | Found | |
|---|---|---|---|
| | $C_{14}H_{15}N_3O_2$ | | |
| C% | 65.37 | 65.02 | 65.18 |
| H% | 5.83 | 5.87 | 5.92 |
| N% | 16.34 | 16.45 | 16.37 |

2.5 g of the thus obtained diphenylamine are introduced in 5 cc of hydrochloric acid ($d = 1.19$) at $-10°$. After 5 minutes of stirring and after washing with 2 cc of iced hydrochloric acid ($d = 1.19$) and drying under vacuum on potash, 3 g of 4-hydroxy 2'-acetylamino 4'-amino diphenylamine dihydrochloride are recovered, the said dihydrochloride melting with decomposition at 263°. Molecular weight calculated for $C_{14}H_{15}N_3O_2 \cdot 2HCl = 330$. Molecular weight found by potentiometric determination in water with 0.1 N soda solution = 322.

EXAMPLE 6

4-hydroxy 2'-acetylamino 4'-N,N-dimethylamino diphenylamine is prepared in accordance with the following reaction:

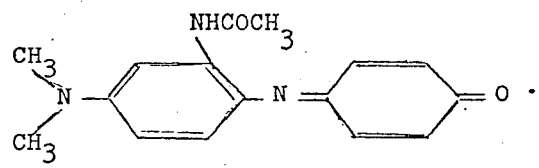

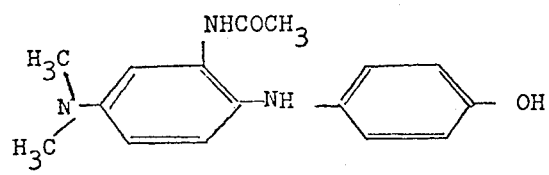

0.025 mole (7 g) of sodium hydrosulfite of 75% purity is dissolved in 80 cc of 0.1 N soda solution. To this solution there is gradually added, with good stirring, while keeping the reaction mixture in the vicinity of 25°, 0.01 mole (3.37 g) of N-[(2'-acetylamino 4'-dimethylamino) phenyl] benzoquinoneimine monohydrochloride monohydrate in 20 cc of 50% dilute ethyl alcohol solution. When the reaction mixture has become colorless, it is cooled to 0° then neutralized with acetic acid to precipitate the above compound which is then filtered under nitrogen, washed with water saturated with carbonic gas and dried under vacuum on phosphoric anhydride. It melts at 204°. Molecular weight calculated for $C_{16}H_{19}N_3O_2 = 285$. Molecular weight found by potentiometric determination in acetic acid by perchloric acid = 282.

| Analysis | Calculated for | Found | |
|---|---|---|---|
| | $C_{16}H_{19}N_3O_2$ | | |
| C% | 67.34 | 67.32 | 67.49 |
| H% | 6.66 | 6.68 | 6.57 |
| N% | 14.73 | 14.72 | 14.64 |

EXAMPLE 7

4-hydroxy 2'-acetylamino 4'-amino 5'-methyl diphenylamine is prepared in accordance with the following reaction:

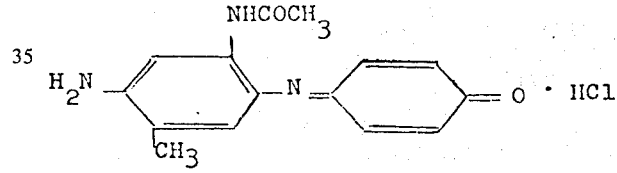

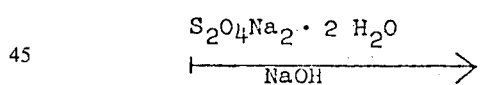

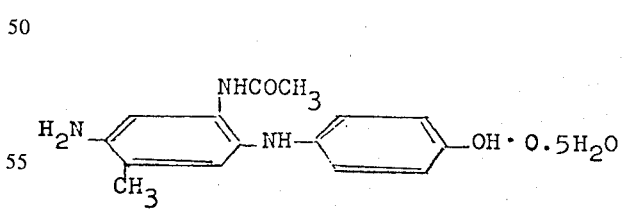

In 100 cc of normal soda solution, there is dissolved 0.028 mole (8.1 g) of sodium hydrosulfite of 75% purity. To this solution there is gradually added, while keeping the temperature in the vicinity of 30°, 0.01 mole (3.05 g) of N-[(2'-acetylamino 4'-amino 5'-methyl) phenyl] benzoquinoneimine hydrochloride in 20 cc of ethyl alcohol and 5 cc of water. When the reaction mixture is colorless, it is cooled to 0°, then neutralized with acetic acid to precipitate the above compound which is then filtered under nitrogen, washed with carbon dioxide gas and dried under vacuum on $P_2O_5$. It melts at 187°. Molecular weight calculated for $C_{15}H_{17}N_3O_2 \cdot 0.5\ H_2O = 280$. Molecular weight found by potentiometric determination in acetic acid by perchloric acid = 277.

| Analysis | Calculated for | Found | |
|---|---|---|---|
| | $C_{15}H_{17}N_3O_2 \cdot 0.5\ H_2O$ | | |
| C% | 64.28 | 64.44 | 64.16 |
| H% | 6.43 | 6.44 | 6.52 |
| N% | 15.00 | 14.89 | 14.73 |

EXAMPLE 8

Alternative method for preparing the 4-hydroxy 3',5'-dimethyl 2',4'-diamino diphenylamine described in Example 2:

0.009 mole (2.65 g) of N-[(2',4'-diamino 3',5'-dimethyl) phenyl] benzoquinoneimine trihydrate is dissolved in 120 cc of water and 250 cc of 95° ethanol. To this solution there are added, drop by drop, at 25°, with stirring, 10 cc of an ammonia solution at 16° Be, previously saturated with hydrogen sulphide. The resulting solution is concentrated under nitrogen to a volume of 150 cc, then cooled to 0°. The above compound is then filtered from the reaction mass, washed with water and then recrystallized in a dimethylformamide-water mixture. After drying under vacuum at 80° for 5 hours, the above compound exhibits a melting point of 220° (no lowering of the melting point is observed when used in mixture with the product prepared in Example 2).

EXAMPLE 9

A hair dye composition is prepared as follows:

| | |
|---|---|
| Compound of Example 1 | 0.1 g |
| Ethanol, 96° titer, | 30 g |
| Water, q.s.p. | 100 g |
| Ammonia at 22°Be, q.s.p. pH 9.5 | |

This dye composition when applied for 20 minutes at ambient temperature to 95% naturally white hair, imparts thereto after rinsing and shampooing, an intense parme shade.

EXAMPLE 10

The following hair dye composition is prepared:

| | |
|---|---|
| Compound of Example 1 | 0.025 g |
| Ethanol, 96° titer | 20 g |
| Water, q.s.p. | 100 g |
| Ammonia at 22°Be, q.s.p. pH 10 | |

This dye composition when applied for 5 minutes at ambient temperature to 95% naturally white hair, imparts thereto, after rinsing and shampooing, a pearly pink beige shade.

EXAMPLE 11

The following hair dye composition is prepared:

| | |
|---|---|
| Compound of Example 1 | 0.05 g |
| 20 volume hydrogen peroxide | 50 g |
| Water, q.s.p. | 100 g |
| Ammonia at 22°Be, q.s.p. pH 10 | |

This dye composition when applied for 20 minutes at ambient temperature to 95% naturally white hair, imparts thereto after rinsing and shampooing, an intense violet shade.

EXAMPLE 12

The following hair-setting lotion composition is prepared:

| | |
|---|---|
| Compound of Example 1 | 0.05 g |
| Vinyl acetate-crotonic acid copolymer (90% vinyl acetate, 10% crotonic acid, molecular weight 45,000 to 50,000) | 1 g |
| Ethyl alcohol, 96° titer | 25 g |
| Water, q.s.p. | 100 g |
| Triethanolamine, q.s.p. pH 7 | |

This hair-setting lotion when applied to bleached hair, imparts thereto a light pearly parme shade.

EXAMPLE 13

The following hair dye composition is prepared:

| | |
|---|---|
| Compound of Example 2 | 0.3 g |
| Ethyl alcohol, 96° titer | 30 g |
| Water, q.s.p. | 100 g |
| 1% lactic acid, q.s.p. pH 4 | |

This hair dye composition when applied for 20 minutes at ambient temperature to bleached hair, imparts thereto after rinsing and shampooing, a very luminous golden pink shade.

EXAMPLE 14

The following hair dye composition is prepared:

| | |
|---|---|
| Compound of Example 2 | 0.2 g |
| Ethyl alcohol, 96° titer | 25 g |
| Water, q.s.p. | 100 g |
| Ammonia at 22°Be, q.s.p. pH 9 | |

This hair dye composition when applied for 20 minutes at ambient temperature to 95% naturally white hair, imparts thereto after rinsing and shampooing, an intense cyclamen pink shade.

EXAMPLE 15

The following hair dye composition is prepared:

| | |
|---|---|
| Compound of Example 2 | 0.005 g |
| Ethyl alcohol, 96° titer | 20 g |
| Water, q.s.p. | 100 g |
| Ammonia at 22°Be, q.s.p. pH 10 | |

This hair dye composition when applied for 20 minutes at ambient temperature to bleached hair, imparts thereto, after rinsing and shampooing, a pearly light blond shade with pink glints.

EXAMPLE 16

The following hair-setting lotion composition is prepared:

| | |
|---|---|
| Compound of Example 2 | 0.1 g |
| Vinyl acetate-crotonic acid copolymer (90% vinyl acetate, 10% crotonic acid, molecular weight 45,000 to 50,000) | 2 g |

| | |
|---|---|
| Ethyl alcohol, 96° titer | 50 g |
| Water, q.s.p. | 100 g |
| Ammonia at 22°Be, q.s.p. pH 7.5 | |

This hair-setting lotion when applied to bleached hair, imparts thereto a golden pink shade.

EXAMPLE 17

The following hair dye composition is prepared:

| | |
|---|---|
| Compound of Example 3 | 0.25 g |
| Ethyl alcohol, 96° titer | 40 g |
| Water, q.s.p. | 100 g |
| Ammonia at 22°Be, q.s.p. pH 10 | |

This hair dye composition when applied for 10 minutes at ambient temperature to 95% naturally white hair, imparts thereto, after rinsing and shampooing, a very luminous pearly pink beige shade.

EXAMPLE 18

The following hair-setting lotion composition is prepared:

| | |
|---|---|
| Compound of Example 3 | 0.05 g |
| Vinyl acetate-crotonic acid copolymer (90% vinyl acetate, 10% crotonic acid, molecular weight 45,000 to 50,000) | 2 g |
| Ethyl alcohol, 96° titer | 50 g |
| Water, q.s.p. | 100 g |
| Ammonia at 22°Be, q.s.p. pH 8.5 | |

This hair-setting lotion when applied to bleached hair, imparts thereto an intense golden shade with pink glints.

EXAMPLE 19

The following hair-setting lotion composition is prepared:

| | |
|---|---|
| Compound of Example 4 | 0.25 g |
| Vinyl acetate-crotonic acid copolymer (90% vinyl acetate, 10% crotonic acid, molecular weight 45,000 to 50,000) | 2 g |
| Ethyl alcohol, 96° titer | 50 g |
| Water, q.s.p. | 100 g |
| Triethanolamine, q.s.p. pH 7.5 | |

This hair-setting lotion when applied to bleached hair, imparts thereto a golden green shade.

EXAMPLE 20

The following hair-setting lotion composition is prepared:

| | |
|---|---|
| Compound of Example 4 | 0.08 g |
| N-[(4'-hydroxy 3',5'-dimethyl) phenyl] 3,5-dimethyl benzoquinoneimine | 0.04 g |
| Vinyl acetate-crotonic acid copolymer (90% vinyl acetate, 10% crotonic acid, molecular weight 45,000 to 50,000) | 2 g |
| Ethyl alcohol, 96° titer | 50 g |
| Water, q.s.p. | 100 g |
| Triethanolamine, q.s.p. pH 7 | |

This hair-setting lotion when applied to bleached hair, imparts thereto an extremely luminous golden blond shade.

EXAMPLE 21

The following hair dye composition is prepared:

| | |
|---|---|
| Compound of Example 3 | 0.05 g |
| 2-amino 4-methoxy phenol hydrochloride | 0.166 g |
| Isopropyl alcohol, 96° titer | 30 g |
| Water, q.s.p. | 100 g |
| Ammonia at 22°Be, q.s.p. pH 8.5 | |

This hair dye composition when applied for 20 minutes at ambient temperature to 95% naturally white hair, imparts thereto, after rinsing and shampooing, a copper blond shade.

EXAMPLE 22

The following hair dye composition is prepared:

| | |
|---|---|
| Compound of Example 3 | 0.25 g |
| 2,6-diamino 4-N,N-diethylamino - phenol trihydrochloride | 0.03 g |
| Isopropyl alcohol, 96° titer | 25 g |
| Water, q.s.p. | 100 g |
| Ammonia at 20°Be, q.s.p. pH 9.5 | |

This hair dye composition when applied for 20 minutes at ambient temperature to 95% naturally white hair, imparts thereto, after rinsing and shampooing, a light bronze shade.

EXAMPLE 23

The following hair dye composition is prepared:

| | |
|---|---|
| Compound of Example 2 | 0.025 g |
| Nitrometaphenylenediamine | 0.075 g |
| Ethyl alcohol, 96° titer | 30 g |
| Water, q.s.p. | 100 g |
| Ammonia at 22°Be, q.s.p. pH 10 | |

This hair dye composition when applied for 20 minutes at ambient temperature to 95% naturally white hair, imparts thereto, after rinsing and shampooing, a very luminous intense golden shade.

EXAMPLE 24

The following hair dye composition is prepared:

| | |
|---|---|
| Compound of Example 5 | 0.4 g |
| Butylglycol | 5 g |
| Lauryl alcohol oxyethylenated with 10.5 moles of ethylene oxide | 5 g |
| Water, q.s.p. | 100 g |

The final pH of this solution is 5.

This hair dye composition when applied for 20 minutes at ambient temperature to 95% naturally white hair, imparts thereto, after rinsing and shampooing, a silvery eucalyptus green shade.

EXAMPLE 25

The following hair dye composition is prepared:

| | |
|---|---|
| Compound of Example 6 | 0.1 g |
| Butylglycol | 5 g |
| Lauryl alcohol oxyethylenated with 10.5 moles of ethylene oxide | 5 g |
| Ammonia at 22°Be, q.s.p. pH 6 | |
| Water, q.s.p. | 100 g |

This hair dye composition when applied for 20 minutes at ambient temperature to bleached hair, imparts thereto, after rinsing and shampooing, a pearly pale green blue shade.

EXAMPLE 26

The following hair dye composition is prepared:

| | |
|---|---|
| Compound of Example 7 | 0.2 g |
| Ethyl alcohol, 96° titer | 25 g |
| Water, q.s.p. | 100 g |
| Ammonia at 22°Be, q.s.p. pH 8 | |

This hair dye composition when applied for 20 minutes at ambient temperature to 95% naturally white hair, imparts thereto, after rinsing and shampooing, a silvery pale green shade.

EXAMPLE 27

The following hair-setting lotion composition is prepared:

| | |
|---|---|
| Compound of Example 5 | 0.2 g |
| Vinyl acetate-crotonic acid copolymer (90% vinyl acetate, 10% crotonic acid, molecular weight 45,000 to 50,000) | 2 g |
| Ethyl alcohol, 96° titer | 50 g |
| Water, q.s.p. | 100 g |
| Triethanolamine, q.s.p. pH 7 | |

This hair-setting lotion when applied to bleached hair, imparts thereto a very intense turquoise blue shade.

EXAMPLE 28

The following hair-setting lotion composition is prepared:

| | |
|---|---|
| Compound of Example 6 | 0.3 g |
| Vinyl acetate-crotonic acid copolymer (90% vinyl acetate, 10% crotonic acid, molecular weight 45,000 to 50,000) | 2 g |
| Ethyl alcohol, 96° titer | 50 g |
| Water, q.s.p. | 100 g |
| Ammonia at 22°Be, q.s.p. pH 6 | |

This hair-setting lotion when applied to bleached hair, imparts thereto a golden pale green shade.

EXAMPLE 29

The following hair-setting lotion composition solution is prepared:

| | |
|---|---|
| Compound of Example 4 | 0.15 g |
| 4-hydroxy-2,4'diamino-5 methyl diphenylamine hydrochloride | 0.06 g |
| Vinyl acetate-crotonic acid copolymer (90% vinyl acetate, 10% crotonic acid, molecular weight 45,000 to 50,000) | 2 g |
| Ethyl alcohol, 96° titer | 50 g |
| Water, q.s.p. | 100 g |
| Ammonia at 22°Be, q.s.p. pH 8.5 | |

This hair-setting lotion when applied to bleached hair, imparts thereto a very luminous pearly beige shade.

We claim:

1. Diphenylamine selected from the group consisting of
a. a diphenylamine of the formula

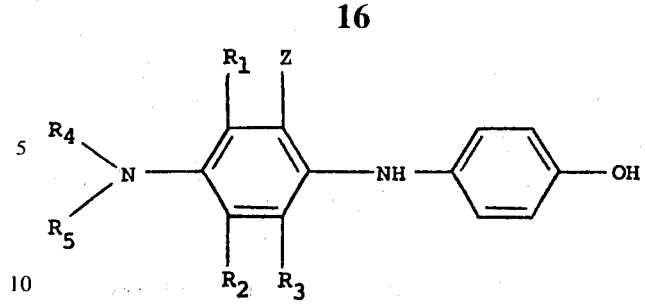

wherein
Z represents a member selected from the group consisting of amino and acetylamino,
$R_1$, $R_2$, $R_4$ and $R_5$ each independently are selected from the group consisting of hydrogen and lower alkyl containing 1-4 carbon atoms and
$R_3$ is hydrogen, with the proviso that at least two of $R_1$, $R_2$, $R_4$ and $R_5$ are other than hydrogen when Z is amino, and
b. an acid salt of said diphenylamine.

2. The diphenylamine of claim 1 wherein said acid salt is the salt of an acid selected from the group consisting of oxalic acid, hydrochloric acid and tartaric acid.

3. A process for preparing the diphenylamine of claim 1 comprising reducing an indoaniline of the formula

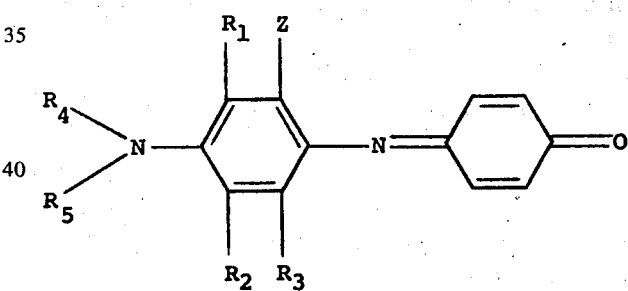

wherein Z and $R_1$ to $R_5$ have the meanings given in claim 1 in a solvent selected from the group consisting of ethanol and ethyl acetate by catalytic hydrogenation at ordinary pressure and at a temperature of 20° to 50°C in the presence of a catalytic amount of palladium on a substrate selected from the group consisting of barium sulfate and carbon, the amount of the palladium on said substrate ranging between about 10 to 25 percent by weight of said indoaniline being reduced.

* * * * *